United States Patent [19]

Akiyama

[11] Patent Number: 4,591,723
[45] Date of Patent: May 27, 1986

[54] OPTICAL EGG INSPECTING APPARATUS
[75] Inventor: Hirokazu Akiyama, Zushi, Japan
[73] Assignee: Q. P. Corporation, Tokyo, Japan
[21] Appl. No.: 706,366
[22] Filed: Feb. 27, 1985
[51] Int. Cl.⁴ .......................................... G01N 21/64
[52] U.S. Cl. .................................................. 250/461.1
[58] Field of Search ........................ 250/458.1, 461.1; 356/407, 417

[56] References Cited

U.S. PATENT DOCUMENTS 2,961,540 11/1960 Jaskowsky et al. ............... 250/461.1
4,516,856 5/1985 Popelka ................................ 356/417

FOREIGN PATENT DOCUMENTS

58-92933 6/1983 Japan ................................. 250/461.1

Primary Examiner—Janice A. Howell
Attorney, Agent, or Firm—Pollock, Vande Sande & Priddy

[57] ABSTRACT

An optical egg inspecting apparatus includes a first transducer unit having a first sensitivity range of 400 to 500 nm in wavelength which corresponds to the absorption spectrum range of yolk (the yellow) and a second transducer unit having a second sensitivity range of 500 to 700 nm in wavelength which corresponds to the visual range excluding the first range. Therefore, the first transducer unit can detect eggshells but cannot detect the yolk, while the second transducer unit can detect both shells or yolk. When the first unit does not detect shells and additionally the second unit detects yolk, the presence of yolk included in egg white is decided even where the egg white includes shells. Further, the two transducer units cannot detect the presence of egg white because a polarized beam projected onto and reflected from egg white to be inspected is shut off by an analyzer having polarization axes arranged perpendicular to those of the polarized beam.

7 Claims, 6 Drawing Figures

OPTICAL EGG INSPECTING APPARATUS

BACKGROUND OF THE INVENTION

1. Field of the Invention

The present invention relates generally to an optical egg inspecting apparatus, and more particularly to an optical egg white (albumin) inspecting apparatus. Egg white is obtained by breaking eggs and then separating egg white from yolk (the yellow of eggs). However, in case yolk is partially included in egg white, it is necessary to eliminate the included yolk from the egg white before feeding the egg white to the succeeding step in food manufacturing processes.

2. Description of the Prior Art

In the food industry, eggs are often used as material for manufacturing confectionery, mayonnaise, dressing, etc. In use of eggs as food material, there exist three different cases: that is, (1) only yolk (the yellow) is used; (2) only egg white is used; and (3) both yolk and egg white are used being included in each other. In any case, first of all eggs should be broken by an egg breaking apparatus. In the first and second cases, yolk and egg white should be separated from each other in egg separating process. At present, the above egg separating process has already been automatized. However, in this egg separating process, there still exists a problem in that yolk is not perfectly separated from egg white or vice versa; that is, some yolk is partially included in egg white. In such a case as described above, the egg white including partial yolk is called a defective egg white, because pure egg white is required for food material. Accordingly, it is indispensable to eliminate the included yolk from egg white before using egg white as food material. To find out the defective egg white including some yolk, conventionally it has been necessary for some workers to visually inspect egg white all the time. The visual inspection makes it difficult to increase egg breaking speed, thus lowering the productivity in food manufacturing process.

In order to automatize the process of detecting the defective egg white, an optical egg white inspecting apparatus which utilizes polarized light has already been proposed. In the prior art apparatus, the presence of yolk is detected on the basis of the following principle. That is, when polarized light is reflected from yolk, the light is scattered by yolk and therefore the polarized light is fairly depolarized; on the other hand, when polarized light is reflected from egg white, the light is little scattered by egg white and therefore the polarized light is less depolarized. The above prior art optical egg white inspecting apparatus will be described in more detail with reference to the attached drawing under DETAILED DESCRIPTION OF THE PREFERRED EMBODIMENT.

In the above prior art egg inspecting apparatus, however, there still exist serious shortcomings. The basic problems are: In the case where eggs are broken by an egg breaking apparatus, a part of an eggshell is inevitably included in egg white. Since the included eggshells are white in color, the polarized light is considerably scattered by the included eggshells and therefore the polarized light is considerably depolarized. That is to say, in case shells are included in the egg white to be inspected, it is impossible to discriminate shells from yolk or vice versa. Therefore, the egg white including shells is determined to be defective in spite of the fact that the egg white includes no yolk. The above shortcomings necessarily reduce the productivity in food manufacturing processes. In this connection, the included eggshells can easily be eliminated by means of filters at a later filtering process.

SUMMARY OF THE INVENTION

With these problems in mind, therefore, it is the primary object of the present invention to provide an egg inspecting apparatus which can automatically and stably detect the defective egg white including yolk even when eggshells are included in the egg white to be inspected.

The principle of discriminating yolk from both egg white and shells is as follows: since shells are white in color and opaque, shells scatter polarized light throughout the visible range (400 to 700 nm). On the other hand, since yolk is yellow in color and opaque, yolk absorbs light having specific wavelengths (400 to 500 nm). On the basis of the above fact, two transducer units are provided, that is, a first transducer unit having a first sensitivity range of 400 to 500 nm in wavelength (absorption spectrum of yolk) and a second transducer unit having a second sensitivity range of 530 to 700 nm in wavelength (visible range excluding the first sensitivity range). The first transducer unit can detect shells but cannot detect yolk; the second transducer unit can detect both shells and yolk simultaneously. Therefore, the presence of yolk included in egg white which includes shells can be detected when the first unit does not detect shells but the second unit detects yolk.

To achieve the above-mentioned object, the egg inspecting apparatus according to the present invention comprises (a) means for projecting a polarized beam onto the egg white to be inspected, (b) means for analyzing light reflected from the egg white to obtain an analyzed beam, polarization axes of said polarized beam projecting means being perpendicular to that of said light analyzing means, (c) means for splitting the analyzed beam into a first split and a second split beam, (d) first means for transducing the first split beam into a first electric signal corresponding thereto, a first sensitivity range of said first transducing means lying within an absorption spectrum range of yolk, (e) second means for transducing the second split beam into a second electric signal corresponding thereto, a second sensitivity range of said second transducing means lying within a range excluding the first sensitivity range, (f) first means for comparing the first electric signal generated from said first transducing means with a first reference level and generating a first comparison signal indicative of presence of shells when the first electric signal exceeds the first reference level, (g) second means for comparing the second electric signal generated from said second transducing means with a second reference level and generating a second comparison signal indicative of presence of shells or yolk when the second electric signal exceeds the second reference level, and (h) means for determining presence of yolk when said first comparing means generates no first comparison signal but said second comparing means generates the second comparison signal.

BRIEF DESCRIPTION OF THE DRAWINGS

The features and advantages of the egg inspecting apparatus according to the present invention over the prior art egg inspecting apparatus will be more clearly appreciated from the following description of the preferred embodiment of the invention taken in conjunction with the accompanying drawings in which like reference numerals designate the same or similar elements or sections throughout the figures thereof and in which.

DETAILED DESCRIPTION OF THE PREFERRED EMBODIMENT

To facilitate understanding of the present invention, a brief reference will be made to a prior art egg inspecting apparatus with reference to the attached drawing.

Figure 1:
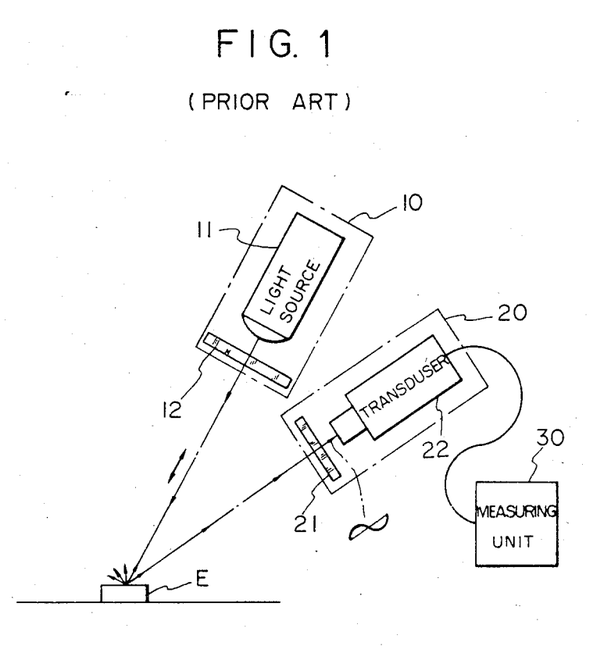
FIG. 1 is a diagrammatical view including a schematic block diagram, which shows an example of a prior art egg inspecting apparatus.

In FIG. 1, the prior art apparatus roughly includes a polarized light source section 10, a photoelectric transducer section 20 and a measuring section 30. The polarized light source section 10 is made up of a light source 11 and a polarizer 12. The photoelectric transducer section 20 is made up of an analyzer 21 and a photoelectric transducer 22. Further, the symbol E denotes part of the egg white to be inspected.

The polarizer affects light (transverse wave radiation) so that the vibrations of the wave are confined to a single plane. In this apparatus, assumption is made that the polarizer 12 transmits linear (plane) polarized light having vibrations confined to planes perpendicular to the sheet and the analyzer 21 transmits linear polarized light having vibrations confined to planes parallel to the sheet. In other words, the direction of polarization axes in the polarizer 12 is perpendicular to that of polarization axes in the analyzer 21. Therefore, when the polarized light transmitted from the polarized light source 10 is reflected perfectly (without being scattered) from the egg white E to be inspected, the transducer section 20 cannot detect the polarized light reflected from the egg white E. Further, the inspecting apparatus is operated under the condition that the polarized light is not subjected to external natural (scattered) light.

Here, since egg white is transparent, the egg white little reflects the incident polarized light into scattered light and therefore little depolarizes the incident polarized light. In other words, the transducer section 20 does not detect the light reflected from the egg white. On the other hand, since yolk is yellow and opaque, the yolk reflects the incident polarized light into scattered light and therefore depolarizes the incident polarized light. In other words, the transducer section 20 detects the light reflected from the yolk.

Therefore, in the case where the egg white E to be inspected includes no partial yolk, the transducer section 20 generates no output signal. In contrast with this, in the case where the egg white E includes partial yolk, the transducer section 20 generates an output signal. In response to the output signal from the transducer section 20, the measuring section 30 outputs an alarm signal, for instance.

In the prior art egg inspecting apparatus as explained above, there exists a problem as follows: In case eggshells are included in egg white, since the included shells are white in color, the polarized light is much scattered and therefore the incident polarized light is depolarized, so that the presence of shells is erroneously detected as the presence of yolk. Further, the egg white including shells is not defective, because the shells can easily be eliminated in the later filtering process.

In view of the above description, reference is now made to an embodiment of the egg inspection apparatus according to the present invention.

Figure 2:
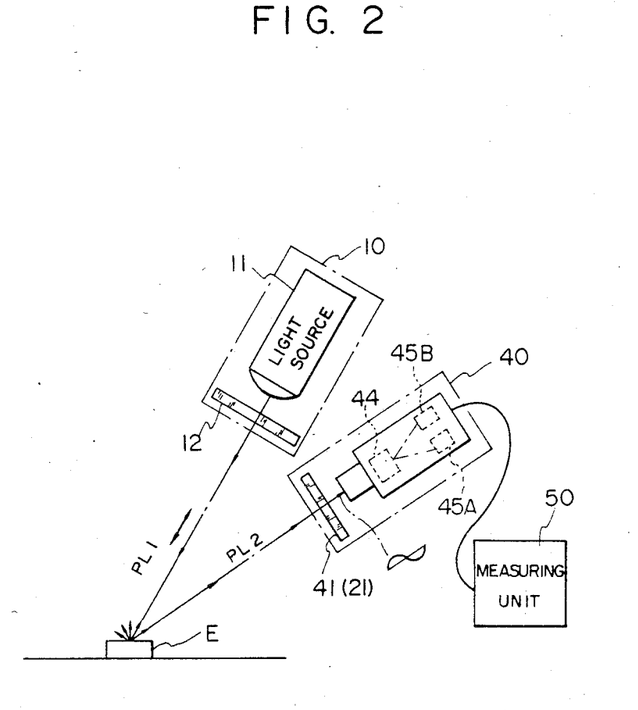
FIG. 2 is a diagrammatical view including a schematic block diagram, which shows an embodiment of the egg inspecting apparatus according to the present invention.
Figure 3:
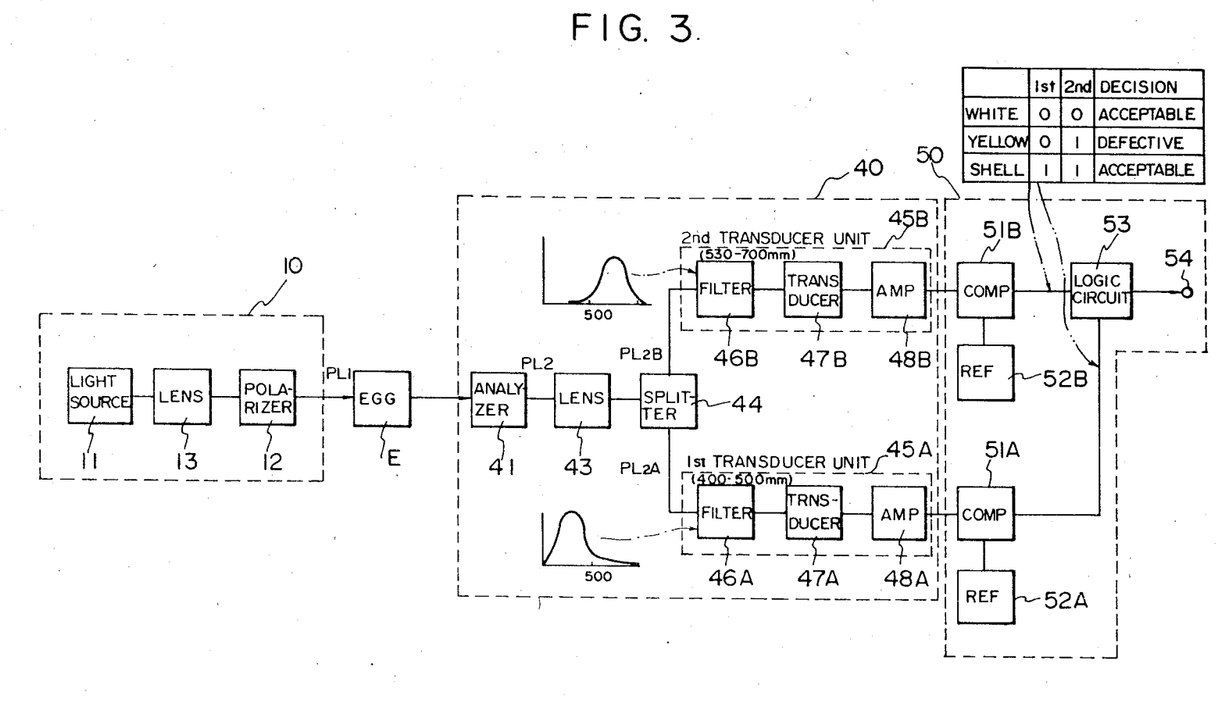
FIG. 3 is a more detailed schematic block diagram of the egg inspecting apparatus according to the present invention shown in FIG. 2.

With reference to FIGS. 2 and 3, the egg inspecting apparatus roughly includes a polarized light source section 10, a photoelectric transducer section 40 and a measuring section 50. The polarized light source section 10 is made up of a light source 11, a light condensing lens 13, and a polarizer 12. The light source 11 is a tungsten lamp, halogen lamp, xenon lamp, high-pressure mercury lamp, etc., for instance, which has a continuous spectrum within the visible region of approximately 400 to 700 nm in wavelength. The light condensing lens 13 collects the light transmitted from the light source 11 into a light beam. The polarizer 12 receives the light beam and transmits a linear (plane) polarized beam $PL_1$ having vibrations confined to planes perpendicular to the sheet, for instance. This polarized beam $PL_1$ is allowed to be incident upon the egg white E to be inspected and then reflected from the egg white E into polarized or scattered light.

The photoelectric transducer section 40 is made up of an analyzer 41, a light condensing lens 43, a beam splitter 44, a first transducer unit 45A (including a first optical filter 46A, a first transducer 47A and a first amplifier 48A), and a second transducer unit 45B (including a second optical filter 46B, a second transducer 47B and a second amplifier 48B). The analyzer 41 receives the polarized or scattered light reflected from the egg white E and transmits linear (plane) polarized $PL_2$ having vibrations confined to planes parallel with the sheet, for instance, that is, perpendicular to the planes confined by the polarizer 12. The light condensing lens 43 collects the polarized light $PL_2$ obtained through the analyzer 41 into a polarized light beam. The beam splitter 44 divides the polarized beam into two separated beams $PL_2A$ and $PL_2B$. A first beam $PL_2A$ is introduced into the first transducer unit 45A; a second beam $PL_2B$ is introduced into the second transducer unit 45B.

The first optical filter 46A is provided with transmission characteristics such that only light having wavelengths of 400 to 500 nm can be passed therethrough. The second optical filter 46B is provided with transmission characteristics such that only light having wavelenghts of 530 to 700 nm can be passed therethrough. The first transducer 47A transduces an optical energy filtered through the first optical filter 46A into an electric energy or a voltage corresponding thereto. The second transducer 47B transduces an optical energy filtered through the second optical filter 46B into an electric energy or a voltage corresponding thereto. As the polarizer 12 and the analyzer 41, it is possible to use any means for polarizing natural light into linear (plane) polarized light, for instance, such as plastic-sheet polarizing plate, polarizing prism, pile-type polarizer, etc. As the optical filters 46A and 46B, it is possible to use trichromatic beam separating color-glass filter, sharp-cut color-glass filter, color-glass filter formed with multi-layer evaporation coating film, etc. As the photoelectric transducers 47A and 47B, it is possible to use photodiodes, phototransistors, photoelectric substances (e.g. Cds), phototubes, photomultiplier tubes, etc.

The measuring section 50 is made up of a first comparator 51A having a first reference (threshold) level presetting device 52A, a second comparator 51B having a second reference (threshold) level presetting device 52B, a logic circuit or decision circuit 53, and an alarm generator 54. The first comparator 51A compares a voltage transduced by the first transducer 47A and amplified by the first amplifier 48A with the first reference level preset by the device 52A and generates a logical "1" signal when the transduced voltage exceeds the first reference level. The second comparator 51B compares a voltage transduced by the second transducer 47B and amplified by the second amplifier 48B with the second reference level preset by the device 52B and generates a logical "1" signal when the transduced voltage exceeds the second reference level.

The logic circuit 53 outputs an "acceptable" signal when both the comparators 51A and 51B generate a logical "1" signal or a logical "0" signal simultaneously, but a "defective signal" when the first comparator 51A generates a logical "0" signal but the second comparator 51B generates a logical "1" signal. In response to the "defective" signal, the alarm generator 54 generates an alarm signal such as alarm light or buzzer, for instance.

Figure 4:
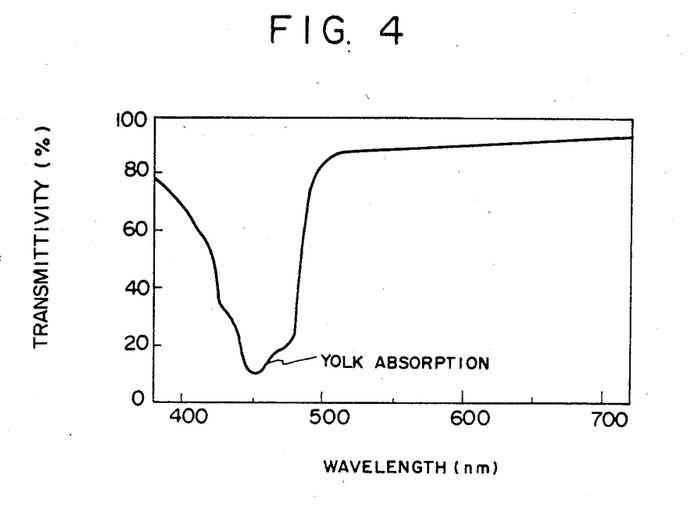
FIG. 4 is a graphical representation showing an example of absorption spectrum or relative transmittivity (intensity ratio of transmitted light to incident light) of yolk.
Figure 5:
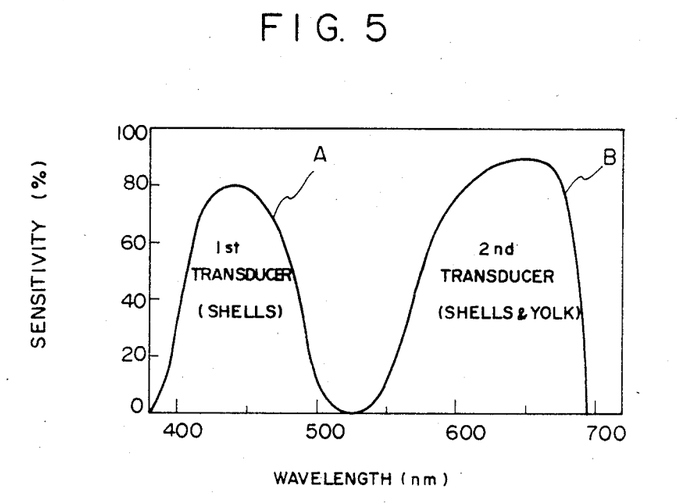
FIG. 5 is a graphical representation showing an example of photosensitivity of two transducer units used with the egg inspecting apparatus according to the present invention.

Prior to description of the operation of the egg inspecting apparatus shown in FIGS. 2 and 3, the basic concept of the present invention will first be described hereinbelow. The inspecting principle is as follows: Since eggshells are white in color, eggshells scatter light throughout the visible region of 400 to 700 nm in wavelength. On the other hand, since yolk is yellow in color, yolk absorbs light having specific wavelengths of 400 to 500 nm. FIG. 4 shows an example of absorption spectrum in yolk, which clearly indicates that there is an absorption peak near 450 nm in wavelength. Further, since egg white is transparent, egg white little scatters light throughout the visible region. On the basis of the above optical nature of egg elements, in the inspecting apparatus according to the present invention, the first transducer unit 45A is so designed that the light sensitivity range lies within a first range of 400 to 500 nm in wavelength, as depicted by symbol A in FIG. 5, which roughly corresponds to the absorption spectrum of yolk shown in FIG. 4. Additionally, the second transducer unit 45B is so designed that the light sensitivity range lies within a second range of 530 to 700 nm in wavelength, as depicted by symbol B in FIG. 5, which roughly corresponds to the visible range excluding the first range A.

By the way, in the prior art egg white inspecting apparatus as shown in FIG. 1, since the transducer section 20 is so designed that the light sensitivity range lies throughout the visible range, it is impossible to discriminate yolk from shells or vice versa. In contrast with this, in the apparatus according to the present invention shown in FIGS. 2 and 3, since two transducer units 45A and 45B are provided separately, it is possible to discriminate yolk and shells by combining the two inspection results of the two transducer units 45A and 45B. In more detail, in the first transducer unit 45A, since the sensitivity range is from 400 to 500 nm, it is impossible to detect the presence of yolk (because yolk absorbs the light having wavelengths lying within this range); however, it is possible to detect the presence of shells (because white shells scatter light throughout the visible range). On the other hand, in the second transducer unit 45B, since the sensitivity range is from 530 to 700 nm, it is possible to detect the presence of yolk (because yolk scatters the light having wavelengths lying within this range) and the presence of shells simultaneously (because shells scatter light throughout the visual range). Therefore, in the case where the two transducer units 45A and 45B simultaneously detect the reflected and polarized beams PL$_2$A and PL$_2$B exceeding each reference level (this indicates the presence of shells), the presence of shells in the egg white to be inspected is determined. On the other hand, in the case where the first transducer unit 45A does not detect the reflected and polarized beam PL$_2$A exceeding the first reference level (this indicates the absence of shells) but the second transducer unit 45B detects the reflected and polarized beam PL$_2$B exceeding the second reference level (this indicates the presence of yolk), the presence of yolk in the egg white to be inspected is determined.

The operation of the egg inspecting apparatus according to the present invention will be described hereinbelow with reference to FIG. 3.

The natural light emitted from the light source 11 is collected by the condensing lens 13 into a beam and linearly polarized through the polarizer 12. The polarized beam PL$_1$ is projected onto the egg white E. The egg E reflects the polarized beam PL$_1$ into scattered light. The reflected and scattered light is linearly polarized again through the analyzer 41 into another polarized light PL$_2$. The polarized light PL$_2$ is collected through the condensing lens 43 into a polarized beam. The polarized beam is then split through the beam splitter 44 into two beams PL$_2$A and PL$_2$B. Here, it should be noted that the polarizer 12 and the analyzer 41 are arranged in such a way that the polarization axes of the polarizer 12 is perpendicular to that of the analyzer 41.

(1) When egg white includes no shells and no yolk:

Since egg white is transparent and does not much scatter the polarized beam PL$_1$, the polarized beam PL$_1$ is not depolarized by the egg white. In other words, the reflected beam is also a beam polarized through the polarizer 12. Since the polarization plane of the analyzer 41 is perpendicular to that of the polarizer 12, the reflected light cannot pass through the analyzer 41, so that the first and second transducer units 45A and 45B do not detect the presence of light beam. Therefore, the transduced voltage signals are both lower than each reference level. Therefore, the first and second comparators 51A and 51B both output a logical "0" signal, simultaneously. The logic circuit 53 generates an "acceptable" signal, and therefore the alarm generator 54 does not generate an alarm signal.

The above case is acceptable because the two transducer units 45A and 45B detect only egg white without detecting the presence of yolk (the yellow) or shells.

(2) When egg white includes only shells:

Since eggshells are opaque and white in color and therefore much scatter the polarized beam PL$_1$ throughout the visible range (400 to 700 nm), the polarized beam PL$_1$ is well depolarized by the shells included in the egg white E. In other words, the reflected beam in no longer a polarized beam but a natural beam having vibrations of waves distributed to various planes. Therefore, part of reflected light can pass through the analyzer 41. The analyzed light PL$_2$ is collected and then split into two beams PL$_2$A and PL$_2$B. In the first transducer unit 45A, the split beam PL$_2$A can pass through the first optical filter 46A having a pass range A of 400 to 500 nm; the passed beam is transduced into an electric voltage signal by the first transducer 47A and then amplified by the first amplifier 48A. Thereafter, the amplified voltage signal is compared with a first reference voltage level generated by the first reference voltage presetting device 52A by the first comparator 51A. Here, the first reference voltage level should be determined to be higher than the amplified voltage signal obtained when the egg to be inspected includes only egg white. In the case where the egg white E includes shells, since the amplified voltage signal will exceed the first reference voltage, the comparator 51A generates a logical "1" indicative of the presence of shells.

On the other hand, in the second transducer unit 45B, the split beam PL$_2$B can also pass through the second filter 46B having a pass range B of 530 to 700 nm; the passed beam is transduced into an electric voltage signal through the second transducer 47B and then amplified by the second amplifier 53B. Thereafter, the amplified voltage signal is compared with a second reference voltage level generated by the second reference voltage presetting device 5B by the second comparator 51B. Here, the second reference voltage level should be determined to be higher than the amplified voltage signal obtained when the egg to be inspected includes only egg white. In the case where the egg white E includes shells, since the amplified voltage signal will exceed the second reference voltage, the comparator 51B generates a logical "1" indicative of the presence of shells. Therefore, the first and second comparators 51A ad 51B output a logical "1" signal, simultaneously. The logic circuit 53 generates an "acceptable" signal or does not generate an alarm signal. The above case is acceptable because the two transducer units 45A and 45B detect shells without detecting the presence of yolk (the yellow). Further, the shells included in the egg white can easily be eliminated by an appropriate filter in the later manufacturing process.

(3) When egg white includes only yolk:

Since yolk is yellow in color and therefore scatters the polarized beam PL$_1$, the polarized beam PL$_1$ is depolarized by the yolk included in the egg white E. In other words, the reflected beam is no longer a polarized beam but a natural beam having vibrations of waves distributed to various planes. Therefore, part of reflected light can pass through the analyzer 41. The analyzed light PL$_2$ is collected and split into two beams PL$_2$A and PL$_2$B. In the first transducer unit 45A; however, the split beam PL$_2$A cannot pass through the first optical filter 46A having a pass range A of 400 to 500 nm. This is because the yolk included in the egg white to be inspected already absorbs the light lying within this range of 400 to 500 nm. Therefore, the first transducer unit 45A does not detect the presence of light beam, and the first comparator 51A outputs a logical "0" signal.

In contrast with this, in the second transducer unit 45B, the split beam PL$_2$B can pass through the second filter 46B having a pass range B of 530 to 700 nm. This is because the yolk reflects the light having wavelengths from 530 to 700 nm. Therefore, the passed beam PL$_2$B is transduced into an electric voltge signal through the second transducer 47B and then amplified by the second amplifier 48B. Thereafter, the amplified voltage signal is compared with the second reference voltage level generated by the second reference voltage presetting device 5B by the second comparator 51B. In case the egg white E includes yolk, since the amplified voltage signal level will exceed the second reference voltage, the comparator 51B generates a logical "1" indicative of the presence of yolk. In other words, the first comparator 51A outputs a logical "0"; however, the second comparator 51B outputs a logical "1", separately. In response to the two different signals, the logic circuit 53 generates a "defective" signal, so that the alarm generator 54 generates an alarm signal such as alarm lamp, buzzer, etc. The above case is defective because the first transducer unit 45A detects the absence of shells but the second transducer unit 45B detects the presence of yolk.

(4) When egg white includes yolk and shells simultaneously:

Since the first and second transducer units 45A and 45B both detect the presence of shells, it is impossible to discriminate the presence of yolk from the presence of shells by the inspecting apparatus according to the present invention shown in FIG. 3. However, the possibility of the simultaneous presence of yolk and shells is very small within a narrow area upon which the polarized beam PL$_1$ is projected to inspect egg white. Therefore, even if the case as described above is disregarded, the quantity of yolk included in egg white may be very small, thus being negligible without deteriorating the quality of egg white.

Further, as explained later with reference to FIG. 6, since the intensity of analyzed beam PL$_2$ obtained due to the presence of shells is greater than that obtained due to the presence of yolk where the diameters of both are the same, it is possible to discriminate shells from yolk or vice versa in dependence upon the difference in output voltage level of the second transducer unit 45B between the two, where necessary. In this case, when the output voltage level of the second transducer units 45B is higher than a third reference level (higher than the first and the second reference levels), the presence of shells is determined; when the same output voltage level is lower than the third reference level, the presence of only yolk is determined.

Figure 6:
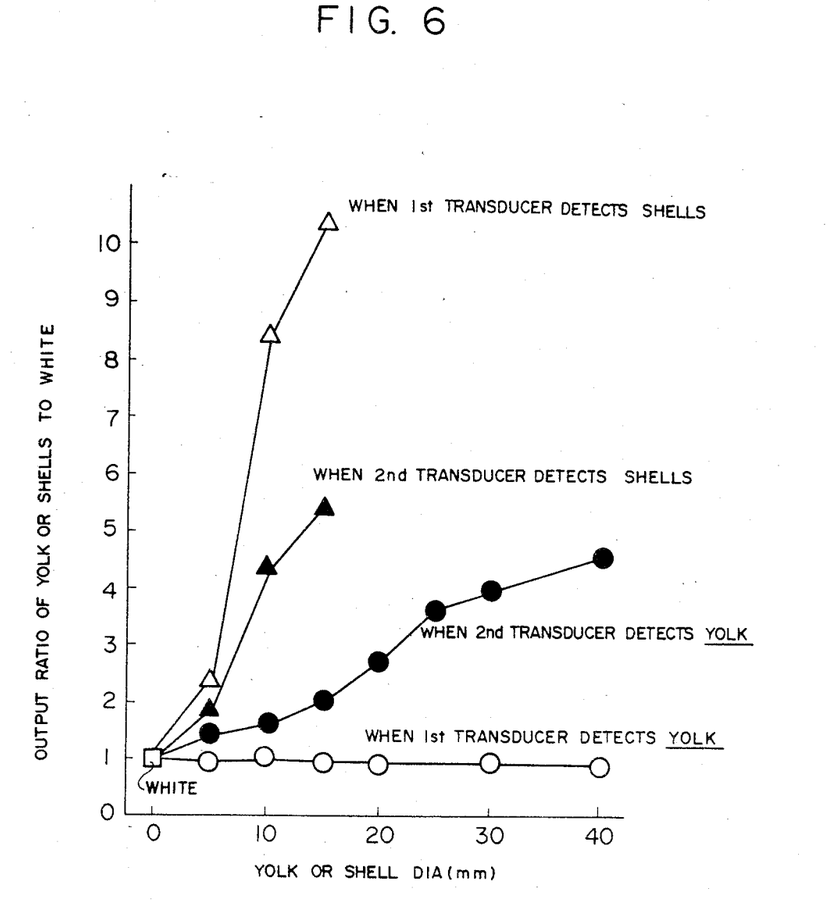
FIG. 6 is a graphical representation showing an example of measurement results obtained by the egg inspecting apparatus according to the present invention shown in FIG. 3.

FIG. 6 is an example of measured results, in which the ratio of transducer output voltage level obtained when yolk or shells are detected to that obtained when only egg white is detected is indicated as ordinate and the diameter of yolk or shell is indicated as abscissa. The above results have been obtained when plastic polarizing sheet is used for the polarizer 12 and the analyzer 41; color glass filter is used for the optical filters 46A and 46B; and the photodiodes are used for the first and second transducers 47A and 47B.

In the graphical representation, a white square represents an output level of 1 obtained when only egg white is detected. Plural white circles represent output levels of roughly 1 obtained when the first transducer unit 45A detects the presence of yolk having different diameters. Plural white triangles represent higher output levels obtained when the first transducer unit 45A detects the presence of shells having different diameters. Plural black circles represent output levels obtained when the second transducer unit 45B detects the presence of yolk having different diameters. Plural black triangles represent output levels obtained when the second transducer unit 45B detects the presence of shells having different diameters. Further, the diameter of shells greater than 15 mm is omitted because of impracticality.

The above graphical representation indicates that: the first transducer unit 45A does not detect the presence of yolk as shown by the white circles. In both the transducer units 45A and 45B, the output level sharply increases with increasing diameter of shells. In the second transducer unit 45B, the output level gently increases with increasing diameter of yolk.

Further, in the prior art egg inspecting apparatus, since only the second transducer unit 45B is provided, the output level increases with increasing diameter of shells or yolk as depicted by black triangles or circles. Therefore, it is impossible to discriminate the both.

Further, as already explained, although the egg inspecting apparatus shown in FIG. 3 cannot detect the presence of yolk when shells are included simultaneously, since the second transducer unit 45B tends to generate a higher transducer output level when shells are detected as compared with when only yolk is detected as depicted by the black triangles and circles in FIG. 6, it is possible to discriminate shells from yolk or vice versa by comparing the second transducer output level with a third reference voltage level.

Furthermore, although the shells included in egg white can easily be eliminated by means of filter at the later process, it is also possible to utilize the present inspecting apparatus for a shell inspecting apparatus. In this case, when both the first and second transducer units 45A and 45B generate high transducer output signals simultaneously, the presence of shells can be determined.

As described above, in the egg inspecting apparatus according to the present invention, since there are provided a first transducer unit having a first sensitivity range of 400 to 500 nm in wavelength which corresponds to the absorption spectrum range of yolk and a second transducer unit having a second sensitivity range of 530 to 700 nm in wavelength which corresponds to the visible range excluding the first sensitivity range, the first transducer unit can detect the presence of shells but cannot detect the presence of yolk, while the second transducer unit can detect the presence of both shells and yolk, simultaneously. Therefore, it is possible to detect only the presence of yolk without detecting the presence of shells by combining these two transducer units. That is to say, the presence of yolk included in egg white including shells can be detected when the first unit does not detect shells but the second unit detects yolk.

In the apparatus according to the present invention, since the presence or absence of yolk included in egg white can be inspected optically and automatically without detecting shells, it is possible to enhance the inspection speed as compared with the conventional visual inspection, thus increasing the speed of egg breaking process and therefore improving the productivity in food manufacturing process.

It will be understood by those skilled in the art that the foregoing description is in terms of a preferred embodiment of the present invention wherein various changes and modifications may be made without departing from the spirit and scope of the invention, as set forth in the appended claims.

What is claimed is:

1. An egg inspecting apparatus for detecting yolk included in egg white, which comprises:
    (a) means (10) for projecting a polarized beam onto the egg white to be inspected;
    (b) means (41) for analyzing light reflected from the egg white to obtain an analyzed beam, polarization axes of said polarized beam projecting means being perpendicular to that of said light analyzing means;
    (c) means (44) for splitting the analyzed beam into a first split beam and a second split beam;
    (d) first means (45A) for transducing the first split beam into a first electric signal corresponding thereto, a first sensitivity range of said first transducing means lying within an absorption spectrum range of yolk;
    (e) second means (45B) for transducing the second split beam into a second electric signal corresponding thereto, a second sensitivity range of said second transducing means lying within a range excluding the first sensitivity range;
    (f) first means (51A) for comparing the first electric signal generated from said first transducing means with a first reference level and generating a first comparison signal indicative of presence of shells when the first electric signal exceeds the first reference level;
    (g) second means (51B) for comparing the second electric signal generated from said second transducing means with a second reference level and generating a second comparison signal indicative of presence of shells or yolk when the second electric signal exceeds the second reference level; and
    (h) means (53) for determining presence of yolk when said first comparing means generates no first comparison signal but said second comparing means generates the second comparison signal.

2. The egg inspecting apparatus as set forth in claim 1, wherein said polarized beam projecting means (10) comprises:
    (a) a light source (11) for emitting a natural light;
    (b) a lens (13) for collecting the emitted natural light into a natural beam; and
    (c) a polarizer (12) for polarizing the natural beam into a polarized beam.

3. The egg inspecting apparatus as set forth in claim 1, wherein said first transducing means (45A) comprises:
    (a) a first optical filter (46A) for passing only light beam having wavelength of 400 to 500 nm; and
    (b) a first photoelectric transducer (47A) for transducing a first optical energy passed through said first optical filter into a first voltage corresponding thereto.

4. The egg inspecting apparatus as set forth in claim 1, wherein said second transducing means (45B) comprises:
    (a) a second optical filter (46B) for passing only light beam having wavelength of 530 to 700 nm; and
    (b) a second photoelectric transducer (47B) for transducing a second optical energy passed through said second optical filter into a second voltage corresponding thereto.

5. The egg inspecting apparatus as set forth in claim 1, wherein said yolk presence determining means (53) is a logical circuit for outputting a logical signal indicative of the presence of yolk in response to a logical "0" signal generated from said first comparing means and a logical "1" signal generated from said second comparing means.

6. The egg inspecting apparatus as set forth in claim 1, which further comprises means (54) for generating an alarm signal when said determining means determines the presence of yolk.

7. A method of detecting yolk included in egg white including shells, which comprises the following steps of:
   (a) projecting a polarized beam confined to first polarization axes onto the egg white to be inspected;
   (b) analyzing the polarized beam reflected from the egg white by second polarization axes perpendicular to the first polarization axes;
   (c) splitting the analyzed polarized beam into a first beam and a second beam;
   (d) filtering a first beam to obtain a first filtered beam having wavelengths of 400 to 500 nm;
   (e) filtering a second beam to obtain a second filtered beam having wavelengths of 500 to 700 nm;
   (f) transducing an optical energy of the first filtered beam into a first voltage corresponding thereto;
   (g) transducing an optical energy of the second filtered beam into a second voltage corresponding thereto;
   (h) comparing the first voltage with a first reference voltage;
   (i) comparing the second voltage with a second reference voltage; and
   (j) determining presence of yolk when the first voltage is lower than the first reference voltage but the second voltage is higher than the second reference voltage.

* * * * *